US007112403B1

(12) United States Patent
Patel et al.

(10) Patent No.: US 7,112,403 B1
(45) Date of Patent: Sep. 26, 2006

(54) METHOD FOR THE IDENTIFICATION OF ANESTHETICS

(75) Inventors: Amanda J. Patel, Juan les Pins (FR); Eric Honore, Juan les Pins (FR); Florian Lesage, Valbonne (FR); Georges Romey, Nice (FR); Michel Lazdunski, Nice (FR); Michel Fink, Bagnols sur Ceze (FR); Fabrice Duprat, Mougins (FR); Francois Maingret, Bristol (GB)

(73) Assignees: Centre National de la Recherche Scientifique, (FR); CNRS and Fabrice Duprat, (FR)

( * ) Notice: Subject to any disclaimer, the term of this patent is extended or adjusted under 35 U.S.C. 154(b) by 0 days.

(21) Appl. No.: 09/503,089

(22) Filed: Feb. 11, 2000

Related U.S. Application Data

(63) Continuation-in-part of application No. 09/144,914, filed on Sep. 1, 1998, now Pat. No. 6,309,855.

(60) Provisional application No. 60/119,727, filed on Feb. 12, 1999.

(51) Int. Cl.
*C12G 3/03* (2006.01)
*C12Q 1/00* (2006.01)
*Q01H 35/08* (2006.01)

(52) U.S. Cl. .................. 435/3; 435/4; 436/55
(58) Field of Classification Search .............. 435/4, 435/3; 436/501, 55; 514/21, 12, 816; 530/350, 530/827
See application file for complete search history.

(56) References Cited

OTHER PUBLICATIONS

Burgess et al "Possible Dissociation of the Heparin-binding and Mitogenic Acitivies of Heparin-binding Growth Factor-1 from Its Receptor-binding Activities by Site-directed Mutagenesis of a single Lysine Residue", Journal of Cellular biology, vol. 111, pp.*
Lazar et al, "Transforming Growth Factor Alpha: Mutation of Aspartic Acid 47 and Leuine 48 Results in Different Biological Activities", Molecular and Cellular Biology, vol. 8, pp. 1247-1252.*
Franks and Lieb, Nature, 1988, vol. 333, pp. 662-664.*
Patel et al (Nature Neuroscience, 1999, vol. 2, pp. 422-426).*
Leonoudakis et al (Journal of Neuroscience, 1998, vol. 18, pp. 868-877).*
Bowie et al (Science, 1990, vol. 257, pp. 1306-1310).*
Nicoll, R.A. and D.V. Madison (1982) General anesthetics hyperpolarize neurons in the vertebrate central nervous system. Science 217, 1055-1077.
Berg-Johnson, J. and I.A. Langmoen (1987) Isoflurane hyperpolarizes neurons in rat and human cerebral cortex. Acta Physiol. Scand. 130, 679-685.
Felisberti, F., B. Antkowiak and K. Kirschfeld (1997) Effects of Volatile anesthetics on the membrane potential and ion channels of cultured neocortical astrocytes. Brain Res. 766, 56-65.

MacIver, M.B. and J.J. Kendig (1991) Anesthetic effects on resting membrane potential are voltage-dependent and agent specific. Anesthesiology 74, 83-88.
Franks, N.P. and W.R. Lieb (1988) Volatile general anesthetics activate a novel neuronal K+ current. Nature 333, 662-664.
Franks, N.P. and W.R. Lieb (1991) Stereospecific effects of inhalational general anesthetic optical isomers on nerve ion channels. Science 254, 427-430.
Winegar, B.D., D.F. Owen, C.S. Yost, J.R. Forsayeth, and E. Mayeri (1996) Volatile general anesthetics produce hyperpolarization of Aplysia neurons by activation of a discrete population of baseline potassium channels. Anesthesiology 85, 889-900.
Fink, M. et al. (1996) Cloning, functional expression and localization of a novel unconventional outward rectifier K+ channel. EMBO J. 15, 6854-6862.
Duprat, F. et al (1997) TASK, a human background K+ channel to sense external pH variations near physiological pH. EMBO J. 16, 5464-5471.
Franks, N.P. and W.R. Lieb (1994) Molecular and cellular mechanisms of general anaesthesia. Nature 367, 607-614.
Fink, M. et al. (1998) A neuronoal two P domain K+ channel stimulated by arachidonic acid and polyunsaturated fatty acids. EMBO J. 17, 3297-3308.
Lesage, F et al (1996) TWIK-1, a ubiquitous human weekly inward rectifying K+ channel with a novel structure. EMBO J. 15, 1004-1011.
Lesage F. et al. (1996) Dimerization of TWIK-1 K+ channel subunits via a disulfide bridge. EMBO J. 15, 6400-6407.
Patel, A. et al (1998) A mammalian two pore domain mechano-gated S-type K+channel. EMBO J. 17, 4283-4290.
Mihic, S.J. et al. (1997) Sites of alcohol and volatile anaesthetic action on GAGA(A) and glycine receptors. Nature 389, 385-389.
Harris, R.A., S.J. Mihic, J.E. Dildy-Mayfied and T.K. Machu (1995) Actions of anesthetics on ligand-gated ion channels: role of receptor subunit composition. Faseb J. 9, 1454-1462.
Yon, J. and M. Fried (1989) Precise gene fusion by PCR. Nucleic Acids Res. 17, 4895.

* cited by examiner

*Primary Examiner*—Karen A. Canella
(74) *Attorney, Agent, or Firm*—DLA Piper (57) ABSTRACT

Human and mouse TREK-1 potassium transport proteins are disclosed as well a method for using potassium transport proteins for identifying substances having anesthetic properties, such as producing a safe, reversible state of unconsciousness with concurrent amnesia and analgesia in a mammal upon inhalation, in a method comprising (a) contacting the test substance with a mammalian potassium transport protein, wherein said potassium transport protein exhibits outward-going potassium rectification; and (b) determining the potassium transport activity of the potassium transport protein, wherein an activation of potassium transport is indicative of the test substance having anesthetic properties.

9 Claims, 5 Drawing Sheets

METHOD FOR THE IDENTIFICATION OF ANESTHETICS

This patent application is a continuation-in-part of application Ser. No. 09/144,914 filed Sep. 1, 1998 now U.S. Pat. No. 6,309,855, which is incorporated by reference in its entirety. This patent application also claims the priority of U.S. Provisional Application No. 60/119,727, filed Feb. 12, 1999.

BACKGROUND OF THE INVENTION

1. Field of the Invention

The invention relates to a method for identifying substances that are capable of acting as anesthetics.

2. Background of the Related Art

Volatile anesthetics are a remarkable class of agents producing a safe, reversible state of unconsciousness with concurrent amnesia and analgesia. They have hyperpolarizing action on mammalian neurons. They activate an inhibitory synaptic $K^+$ current ($I_{K(An)}$) in molluscan pacemaker neurons which has been proposed to have an important role in general anaesthesia.

Volatile anesthetics hyperpolarize frog motor neurons, rat hippocampal neurons, guinea pig thalmic neurons and human cerebral cortex neurons. Therefore, it has been proposed that the molecular mechanism of volatile anesthetics involves an action on a specific class of K+ channels. The fact that a particular inhibitory synaptic K+ current, $I_{K(An)}$, reversibly activated by volatile agents is present in anesthetic-sensitive molluscan pacemaker neurons, but absent in insensitive neurons has made it a very attractive candidate as a target for these important pharmacological agents. $I_{K(An)}$ behaves as a background channel; it is not voltage-gated, it activates immediately, and it does not inactivate with time. $I_{K(An)}$ obeys the Goldman-Hodgkin-Katz constant field equation and is resistant to the classical K+ channel blockers, tetraethylammonium and 4-aminopyridine.

Figures 1A, 1B, 1C, 1D, 1E:
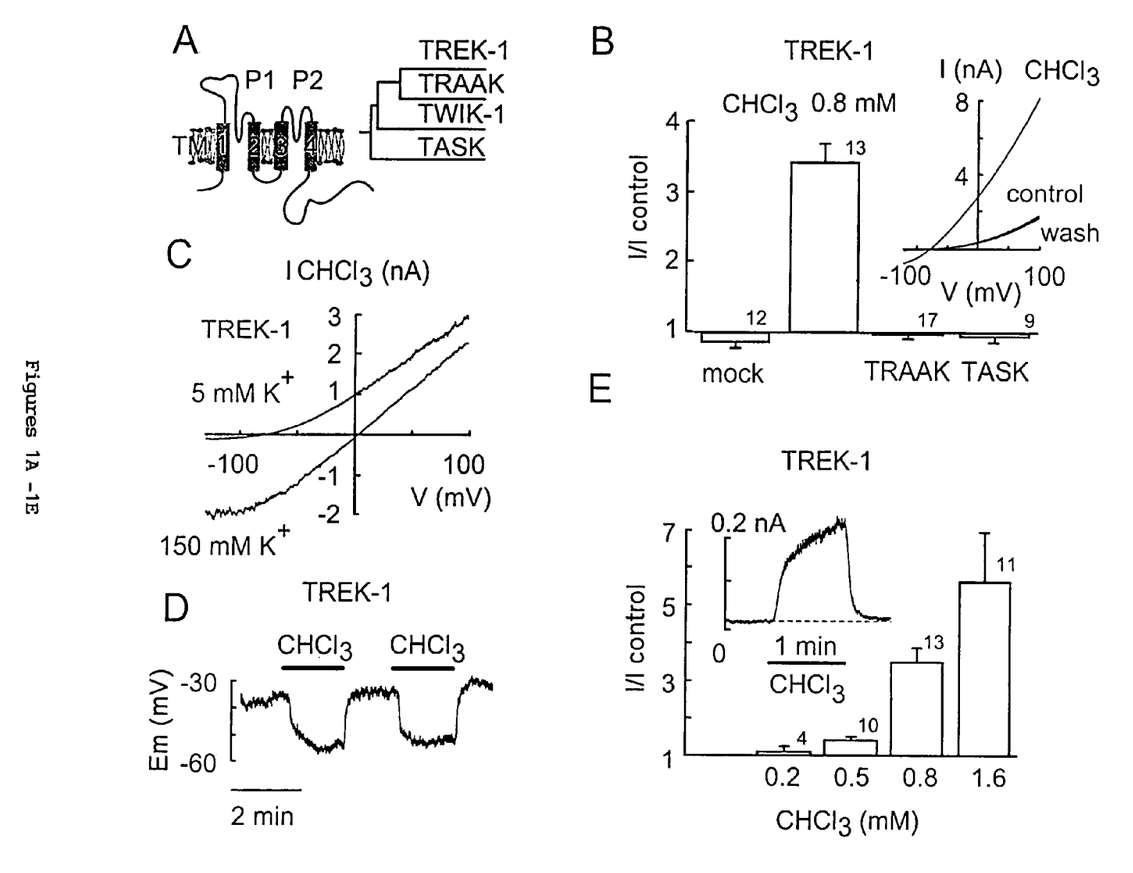

We recently identified a novel family of mammalian K+ channels with a unique structural motif consisting of two pore domains in tandem and four transmembrane segments. The four members in this family have been classified as TWIK-1, TASK, TREK-1, and TRAAK, which are shown in FIG. 1A. TWIK-1 has been previously shown to dimerize, implying that a functional channel is formed by at least two subunits. Heteromultimerization does not occur between the four members of this novel family as tested in Sf9 cells expressing various combinations of these channels (unpublished data). Three members of this family, mouse TREK-1, mouse TRAAK, and human TASK, encode for background outward-going K+ rectifiers with properties resembling those of $I_{K(An)}$. TRAAK and TREK-1 are directly opened by arachidonic acid and other polyunsaturated fatty acids, while TASK encodes a resting K+ channel which is controlled by external pH variations near physiological pH. TREK-1 and TASK are expressed in many tissues and are particularly abundant in the brain and in the heart, whereas TRAAK is selectively expressed in the central nervous system. Neuronal expression of these channels is detected at high levels in the cortex, cerebellum, hippocampus and olfactory bulb, and cardiac expression is detected in both the myocardium and connective tissues.

BRIEF DESCRIPTION OF THE FIGURES

FIG. 1 shows the results of experiments with chloroform demonstrating that chloroform selectively activates TREK-1: A, a schematic showing the two pore domains and four transmembrane domains of the 2P domain potassium K+ channels, TREK-1 TRAAK, TWIK-1 and TASK. The four transmembrane domain segments are indicated by TM1 through TM4, and the two pore regions are indicated by P1 and P2. The phylogenetic tree indicates the three subfamilies. TWIK-1 is an inward rectifier K+ channel and TASK is a background rectifier K+ channel inhibited by external acidosis. Both TREK-1 and TRAAK are background outward rectifier K+ channels opened by arachidonic acid; B, whole cell patch clamp experiments showing that 0.8 mM chloroform strongly and reversibly activates TREK-1 expressed in transfected COS cells. The mock condition is the wild-type (empty) expression vector. The effects of chloroform were investigated on K+ currents elicited in the whole cell configuration during a voltage ramp of one second in duration from a holding potential of −80 mV as illustrated in the inset for TREK-1; C, 0.8 mM chloroform induced a typical background current characterized by an outward-going rectification which reverses at the predicted value for $E_{K+}$; Chloroform activated TREK-1 currents in physiological and symmetrical K+ gradients were examined. Voltage ramps of one second in duration from a holding potential of −80 mV in both K+ conditions and in the presence of 0.8 mM chloroform were digitally subtracted from ramps in control conditions; D, 0.8 mM chloroform reversibly and reproducibly hyperpolarized COS cells expressing TREK-1; E, dose-dependence of TREK-1 activation. The inset illustrates the effect of 0.8 mM chloroform on TREK-1 current measured at a holding potential of 0 mV. The number of cells in each experimental condition is indicated.

FIG. 2 Halothane is a common activator of TREK-1 and TASK. A, comparative effects of 1 mM halothane on the 2P domain K+ channel activities. The mock condition is the wild-type (empty) expression vector; B, halothane (1 mM) stimulates TASK channel activity elicited in the whole cell configuration during voltage ramps of one second in duration from a holding potential of −80 mV; C, halothane (1 mM)-activated TASK currents in physiological and symmetrical K+ gradients. Voltage ramps of one second in duration from a holding potential of −80 mV in both K+ conditions and in the presence of 1 mM halothane are digitally subtracted from ramps in control conditions; D, dose-effect curve of halothane on TREK-1 channel activation; F, halothane (1 mM) reversibly activates TASK at a holding potential of 0 mV. The number of cells in each experimental condition is indicated.

FIG. 3 Isoflurane and diethyl ether differentially activate TREK-1 and TASK. A, comparative effects of 2 mM isoflurane (A) and 0.6 mM diethyl ether (B) on the 2P domain K+ channels. The mock condition is the wild-type (empty) expression vector. The effects of the anesthetics are investigated on K+ currents elicited in whole cell configuration during voltage ramps of one second in duration from a holding potential of −80 mV as illustrated in insets for TREK-1. The number of cells in each experimental condition is indicated.

FIG. 4 Volatile anesthetics stimulate TREK-1 and TASK in the excised patch configurations. A, effects of increasing concentrations of halothane on TREK-1 channel activity in an outside-out patch. In an outside-out patch, halothane reversibly opens a 48 pS TREK-1 channel in a dose-dependent fashion. The holding potential is 0 mV and applications of halothane are indicated by horizontal bars; B, effect of 0.8 mM chloroform on the I-V curve of TREK-1 in an outside-out patch. The I-V curve is performed with a voltage ramp of one second in duration from a holding potential of −80 mV; C, kinetics of activation of TREK-1 by 0.8 mM chloroform. The I-V curve of the chloroform-sensitive current in an outside-out patch shows the characteristic outward-going rectification; D, halothane (1 mM) induces TASK channel opening in an inside-out patch. The holding potential is 0 mV and channel activities before, during, and after addition of 1 mM halothane are illustrated from left to right. Halothane reversibly opens a 12 pS TASK channel.

FIG. 5 Functional characterization of the human TREK-1 (hTREK-1). Transiently transfected COS cells expressing hTREK-1 are voltage-clamped using the whole cell patch clamp configuration. A, The basal TREK-1 current is recorded in physiological K conditions (5 mM) and in symmetrical K conditions (155 mM). The cells are held at −80 mV and voltage ramps of 800 ms in duration are applied from −130 mV to 100 mV. B, hTREK-1 is stimulated by the addition of 10 μM arachidonic acid in the bath. Same protocol as in A. C, hTREK-1 is opened by increasing concentrations of halothane (as indicated). D, In the inside-out patch configuration hTREK-1 is opened by a membrane stretch of −66 mmHg. The patch is voltage clamped at 0 mV.

SUMMARY OF THE INVENTION

The invention relates to human TREK-1, its nucleotide and amino acid sequence. The invention further relates to murine TREK-1, its nucleotide and amino acid sequence.

Thus, the invention relates to a method for the identification of substances that activate potassium transport through a potassium transport protein, including TREK-1 and TASK. The potassium transport proteins activated in the method exhibit outward-going rectification. Specifically, the method involves contacting a substance to be tested with a mammalian transport protein and examining the potassium transport activity of the potassium transport proteins. A positive result, activation of potassium transport, correlates with a substance which produces anesthesia.

DETAILED DESCRIPTION OF THE INVENTION

The invention is an isolated nucleic acid molecule encoding the human TREK-1 channel (SEQ ID NO:1). The invention is also embodied in the isolated human TREK-1 protein (SEQ ID NO:2). The nucleic acid and deduced amino acid sequence is shown in SEQ ID NO:1.

The invention also encompasses the isolated nucleic acid molecule encoding the murine TREK-1 channel (SEQ ID NO:3). The isolated protein, murine TREK-1 (SEQ ID NO:4), is also encompassed by the invention.

The method involves contacting a test substance with a potassium transport protein in vitro and determining whether there has been activation of potassium transport.

As used in the method, cells which express a potassium transport protein are used in the presence of the test substance. The test substance is a substance which will have certain properties when used in a mammal as a volatile inhalant. These properties may include the induction of a safe, reversible state of unconsciousness, amnesia and analgesia.

The cells expressing the potassium transport protein may transiently express the protein or constitutively express the protein. The cells may be of any type which can express the protein in appropriate conformation to allow for the transport of potassium. Examples of such cells include, mammalian cells, vertebrate cells, and invertebrate cells. Examples of mammalian cells suitable for use in the invention include, but are not limited to, cells of neuronal origin, fibroblasts, myocardial cells, COS cells, Chinese hamster ovary (CHO) cells, embryonic kidney cells, fibroblasts, HeLa cells, and the like. Examples of suitable non-mammalian vertebrate cells include, but are not limited to frog oocytes, such as *Xenopus laevis* oocytes, and the like. Suitable invertebrate cells include, but are not limited to, insect cells, such as *Spodoptera frugiperda* (Sf9) cells, and the like. Any cell known in the art which may be transfected to transiently or constitutively express the transport protein are suitable for use in the present invention.

The potassium transport proteins which are suitable for use in the invention include TREK-1 (SEQ ID NO:2 and SEQ ID NO:4) and TASK (SEQ ID NO:5), which may be derived from any mammalian source, such as rat, mouse, or human. The molecular sequence of TREK-1 may be the human TREK-1 as shown in SEQ ID NO:2, or an amino acid sequence that is substantially identical to SEQ ID NO:2. By "substantially identical" it is understood that amino acid substitutions may be made such that the overall conformation of the potassium transport protein is not significantly altered: the protein remains active as a potassium transport protein.

A suitable substantially identical protein is a protein having an amino acid sequence that is generally at least 90% identical to the amino acid sequence of human TREK-1 (SEQ ID NO:2). More preferably, the protein is at least 95% identical to SEQ ID NO:2. Most preferably, the amino acid sequence is at least 99% identical to SEQ ID NO:2.

The cells used in the method of the present invention express the potassium transport protein expressed on their surface, either constitutively or transiently. Introduction of the nucleic acid into the cells so that the protein is expressed may be by any known method such as transfection of an appropriate nucleic acid construct into the cells, microinjection of RNA encoding the protein, and the like. Many different protocols are known in the art. Two methods are briefly described herein, however, it will be appreciated by one of ordinary skill in the art that many modifications and substitutions may be made to these methods without departing from the spirit and the scope of the invention.

The coding sequence of the potassium transport protein may be inserted between the noncoding sequences 5' and 3' of a *Xenopus laevis* protein (such as globin) in an appropriate vector, such as pEXO. The construct is introduced into an appropriate cell type to replicate the vector and/or to transcribe RNA. Alternatively, the vector may be used as a template for in vitro transcription. A complementary RNA (cRNA) is transcribed and injected into a cell, such as a *Xenopus* oocyte. Such a procedure may be performed in a 0.3 ml perfusion chamber, wherein single oocytes are impaled on two standard glass microelectrodes (0.5–2.0 MW) charged with 3 M KCl and maintained under voltage clamp with a Dagan TEV200 amplifier. The bath solution contains 98 mM KCl, 1.8 mM $CaCl_2$, 2 mM $MgCl_2$, and 5 mM HEPES at pH 7.4 with KOH.

Alternatively, functional expression of the potassium channel may be accomplished by transfection of insect cells, such as *Spodoptera frugiperda* (Sf9) cells. Briefly a suitable vector, such as pVL1392 may be used and the coding sequence for the potassium transport protein may be inserted into the vector in-frame so that expression of the potassium transport protein may be expressed. The coding sequence for the potassium transport protein may be obtained by any convenient method, such as by PCR or by digesting a plasmid containing the potassium transport protein coding sequence with appropriate restriction endonuclease(s) for subsequent ligation into the pVL1392 vector. Similarly, the amplified product of the PCR may be digested with restriction enzymes and ligated into the vector. Transfection of Sf9 cells may be performed by the manufacturer's protocol (Pharmingen).

Alternatively, functional expression of the potassium channel may be by transient transfection of cells such as COS cells whereby COS cells are seeded at a density of 20,000 cells per 35 mm dish. Cells are transfected with expression vector, such as the pIRES-CD8 vector, comprising the nucleic acid molecules encoding the desired potassium channel protein. The cells may be transfected by any method known in the art, such as the DEAE dextran protocol, $Ca_2PO_4$ precipitation, or electroporation, for example. The transfected cells, expressing the desired potassium channel, or induced to express the desired potassium channel may then be used in the method of the invention and the cells may be assayed for the transport of potassium.

The invention will be described in greater detail with reference to the examples which are provided to illustrate the invention. The examples are not to be construed to be limiting as to the scope of the invention, which is set forth in the appended claims.

EXAMPLES

1. Cloning of the Human TREK-1 Channel

The TREK-1 channel was cloned by degenerate PCR technology using previously characterized murine sequence. Although such technology is extensively described in the literature and is familiar to those of ordinary skill in the art, briefly, degenerate oligonucleotide primers selected to amplify a region of murine TREK-1 were synthesized and placed in a polymerase chain reaction amplification using human DNA with appropriate buffer, nucleotides and DNA polymerase. The reaction is cycled through temperature stages for denaturation of DNA (generally about 94° C.), annealing of primers to DNA template (this temperature can be varied to optimize amplification and can be based on many factors, including primer length and GC content), and extension of DNA polymerization by DNA polymerase (generally at the optimum temperature for the activity of the DNA polymerase which is usually about 72° C.). The amplified DNA fragment may be isolated and cloned into a plasmid vector for subsequent sequence analysis, or the amplified DNA may be directly sequenced by known methods.

Due to the degeneracy of the DNA code, it will be well understood to one of ordinary skill in the art that substitution of nucleotides may be made without changing the amino acid sequence of the protein. Therefore, the invention includes any nucleic acid sequence for the human TREK-1 channel that encodes the amino acid sequence determined for human TREK-1 (SEQ ID NO:2). Moreover, it is understood in the art that for a given protein's amino acid sequence, substitution of certain amino acids in the sequence can be made without significant effect on the function of the protein. Such substitutions are known in the art as "conservative substitutions." The invention encompasses human TREK-1 proteins that contain conservative substitutions, wherein the function of the protein is not altered. Generally, the identity of such a mutant TREK-1 will be at least 90% identical to SEQ ID NO:2. Preferably, the mutant TREK-1 will be at least 95% identical to SEQ ID NO:2. More preferably, the mutant TREK-1 will be at least 97% identical to SEQ ID NO:2. Most preferably, the mutant TREK-1 will be at least 99% identical to SEQ ID NO:2.

2. The Sequencing of the Murine TREK-1 Channel

The sequence for murine TREK-1, which is a corrected form of murine TREK-1 reported earlier, is shown in SEQ ID NO:4. There is a longer open reading frame than originally reported, producing a protein with a deduced amino acid sequence of 411 amino acids. Due to the degeneracy of the DNA code, it will be well understood to one of ordinary skill in the art that substitution of nucleotides may be made without changing the amino acid sequence of the protein. Therefore, the invention includes any nucleic acid sequence for the murine TREK-1 channel that encodes the amino acid sequence determined for murine TREK-1 (SEQ ID NO:4). Moreover, as is the case with human TREK-1, it is understood in the art that for a given protein's amino acid sequence, substitution of certain amino acids in the sequence can be made without significant effect on the function of the protein. The invention encompasses murine TREK-1 proteins that contain conservative substitutions, wherein the function of the protein is not altered. Generally, the identity of such a mutant TREK-1 will be at least 90% identical to SEQ ID NO:4. Preferably, the mutant TREK-1 will be at least 95% identical to SEQ ID NO:4. More preferably, the mutant TREK-1 will be at least 97% identical to SEQ ID NO:4. Most preferably, the mutant TREK-1 will be at least 99% identical to SEQ ID NO:4.

3. Functional Expression of the Human TREK-1 Channel

Figure 5A:
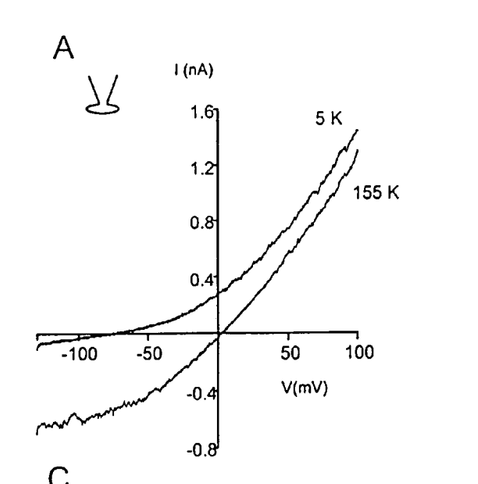
Figure 5B:
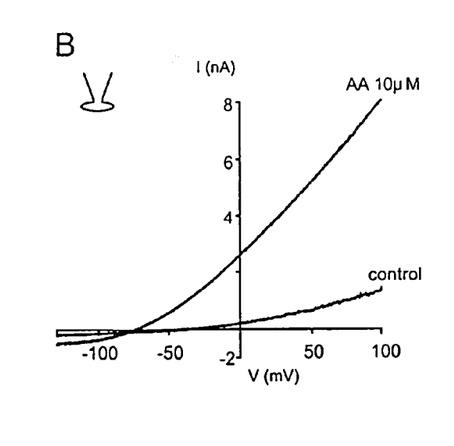
Figure 5C:
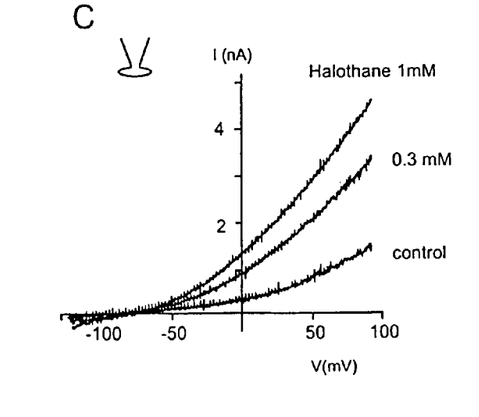
Figure 5D:
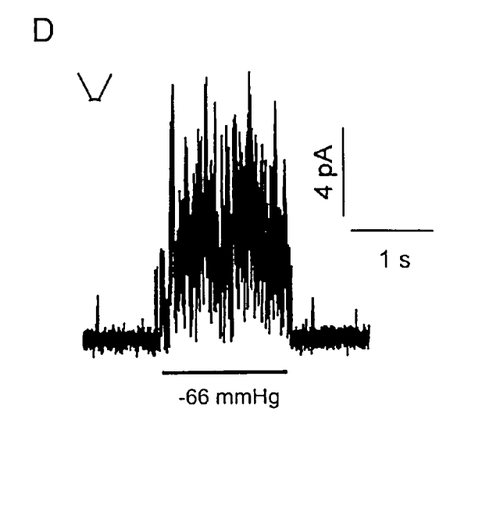

The functional properties of the human TREK-1 channel were studied on the basis of transfected COS cells temporarily expressing the protein. Like the murine channel, the human channel is selective for potassium and is activated by cis-unsaturated fatty acids, volatile anesthetics and by stretching of the plasma membrane. The selectivity of the TREK-1 currents for potassium is shown in FIG. 5A. The currents are recordings in the whole-cell configuration of the patch-clamp technique (imposed potential gradient from −130 to +100 mV). The inverse potential of the currents follow the equilibrium potential of potassium when the extracellular concentration of potassium ions climbs from 5 to 155 mM. FIG. 5B shows that the application of arachidonic acid (10 μM) induced activation of the TREK-1 currents. FIG. 5C shows that the application of volatile anesthetics (halothane in this case) at the concentrations employed in general anesthesia induced activation of the TREK-1 channel. FIG. 5D shows that the TREK-1 currents recorded in an excised patch (inside-out configuration) are mechanosensitive. When a pressure of −66 mmHg is applied on the membrane, the TREK-1 currents are activated in a reversible manner.

4. Electrophysiological Recording

COS cell transfection, culture and electrophysiology are well known in the art and are described in the literature such as in the references cited.

As performed herein, COS cells were seeded at a density of 20,000 cells per 35 mm dish 24 hours prior to transfection. Cells were transfected by the DEAE dextran protocol (1 μg DNA per plate). Mouse TREK-1 (GenBank Accession No. U73488), human TASK (GenBank Accession No. AF006823) and mouse TRAAK (GenBank Accession No. AF056492) fragments were amplified by polymerase chain reaction (PCR) and subcloned into the pIRES-CD8 vector. Transfected cells were visualized 48 hours after transfection using the anti-CD8 antibody coated beads method. For whole cell and excised patch experiments, the internal solution was 150 mM KCl, 3 mM MgCl$_2$, 5 mM EGTA and 10 mM HEPES at pH 7.2 with KOH and the external medium contained 150 mM NaCl, 5 mM KCL, 3 mM MgCl$_2$, 1 mM CaCl$_2$, 10 mM HEPES at pH 7.4 with NaOH. Cells were continuously superfused with a microperfusion system during the time course of the experiments (0.1 ml/min) performed at room temperature. A RK300 patch clamp amplifier (Biologic, Grenoble, France) was used for whole cell as well as single channel recordings. Ionic currents were monitored and recorded continuously using a DAT recorder (Biologic, Grenoble, France). Subsequently, data were replayed and sampled using pClamp software. Data analysis were performed using clampfit (pClamp) for whole cell recording as well as Biopatch (Biologic) software for single channel recordings. Membrane capacitance was measured during a 10 V hyperpolarizing step from a holding potential of −80 mV. Student's t test was used for statistical analysis (P<0.001).

5. Anesthetics Delivery and Concentration

General anesthetics were directly dissolved in saline solutions. All experiments were performed at room temperature (24° C.). Solutions were prepared every 3 hours in gas-tight bottles as stock solutions (calculated concentrations of 510 mM). Serial dilutions were prepared just prior to the electrophysiological experiment. 2.5 ml of each experimental solution at the desired concentration was placed in a syringe connected to the experimental superfusion system. The electrophysiological measurements were performed within 45 minutes.

The actual concentrations of anesthetics were subsequently determined by means of a gas chromatography method (HP 6890 equipped with a DB624 column) using FID detection. Samples (2.5 ml of solution) were collected prior to ($t_0$) and after perfusion ($t_{45}$) through the experimental setup. Solutions were collected using gas impermeable tubing and stored in sealed glass containers at 4° C. for subsequent analysis. Samplings and measurements were performed in duplicate. Actual concentrations of anesthetics were determined by multiplying the calculated concentration by the ratio $t_{45}/t_0$ (chloroform: 0.16; halothane: 0.37, isoflurane: 0.76; and diethyl ether: 0.57). In the dose effect curves, the threshold concentrations were estimated as concentrations producing an increase higher than 10% in current amplitude.

Results

The nucleic acid sequence corresponding to the open reading frame of the human TREK-1 channel is shown in SEQ ID NO:1. The sequence of 1236 nucleotides encodes a protein of 411 amino acids. The conservation between human and murine proteins is very high, exceeding 99% homology.

TASK and TREK-1, two mammalian 2P domain K+ channels which have similar properties to $I_{K(An)}$ are activated by volatile general anesthetics. Chloroform, diethyl ether, halothane and isoflurane activated TREK-1, while only halothane and isoflurane activated TASK. The C-terminal regions of both TREK-1 and TASK are critical for anesthetic activation. Thus, both TREK-1 and TASK are important target sites for these agents.

In whole patch clamp experiments shown in FIG. 1B, chloroform strongly and reversibly activated TREK-1 expressed in transfected COS cells, while it slightly depressed TASK and did not effect TRAAK. As shown in FIG. 1C, chloroform induced a typical background current, characterized by an outward-going rectification which reverses at the predicted value for $E_K^+$ as demonstrated by the shift of the reversal potential to 0 mV in symmetrical K$^+$ conditions. No current activation was observed in mock-transfected cells (FIG. 1B). FIG. 1D shows that chloroform also reversibly and reproducibly hyperpolarized COS cells expressing TREK-1 (but not mock-transfected cells, not shown; n=5). TREK-1 activation was dose dependent, with a threshold concentration for activation of 500 µM, as shown in FIG. 1E. The inset of FIG. 1E shows that current activation, measured at a holding potential of 0 mV, started rapidly, but steady-state activation was barely reached after one minute in the presence of chloroform.

Figure 2A:
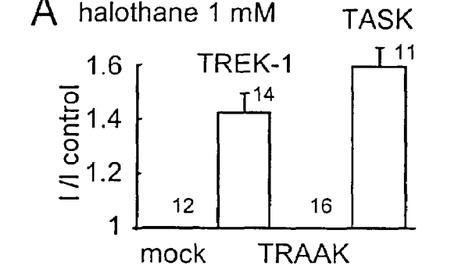
Figure 2B:
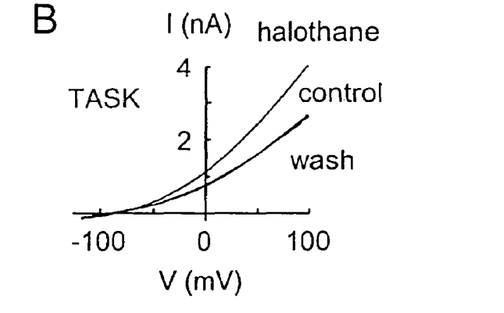
Figure 2C:
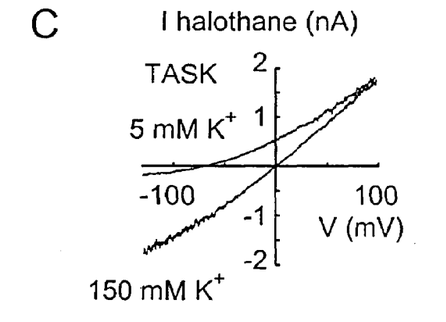
Figure 2D:
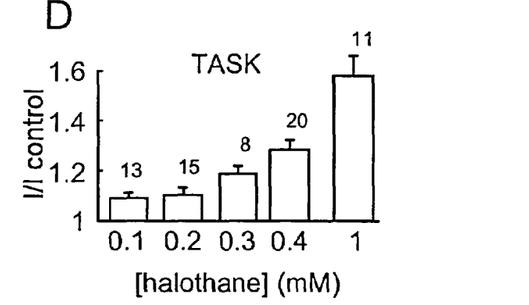
Figure 2E:
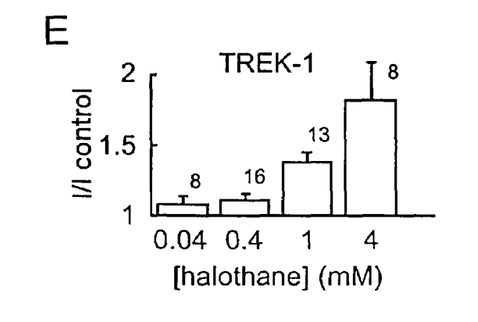
Figure 2F:
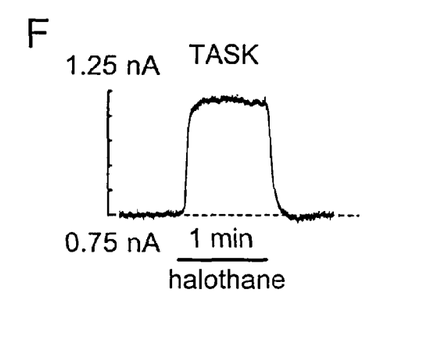

Both TREK and TASK, but not TRAAK, were opened by halothane. As shown in FIGS. 2B and 2C, halothane-induced current displayed an outward-going rectification and revered at the predicted value for $E_K^+$. The dose-effect curves (shown in FIG. 2D and FIG. 2E) demonstrated that the threshold concentrations for halothane on TREK-1 and TASK are 400 µM and 200 µM, respectively. The effects of halothane on TASK were rapid completely reversible. Opening of TASK was faster compared to the opening of TREK-1 by chloroform (compare FIG. 2F with FIG. 1E, inset). These results suggest that the components of the activation of both channels by anesthetics may be mediated by different molecular mechanisms.

Figure 3A:
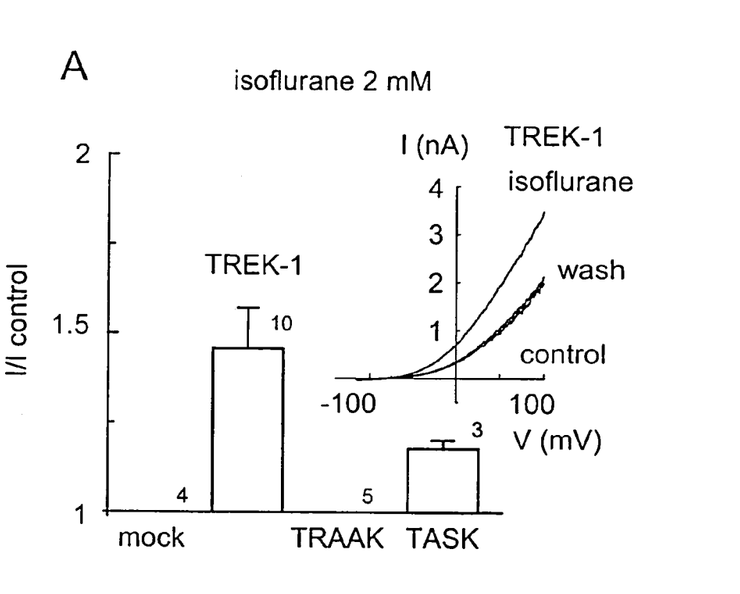
Figure 3B:
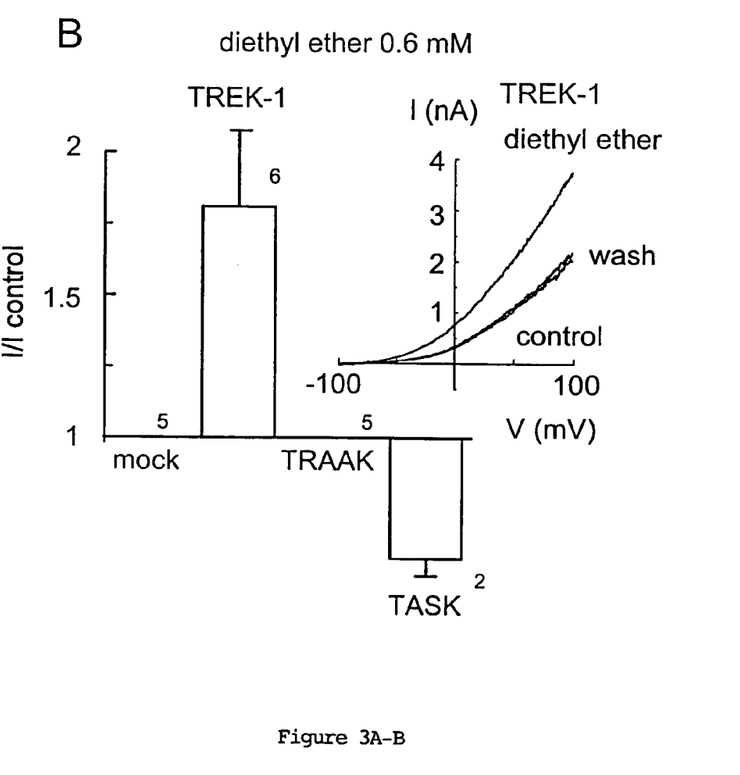

Isoflurane, like halothane, activated both TREK-1 and TASK channels without altering TRAAK, as shown in FIG. 3A. Diethyl ether, like chloroform, opened TREK-1, but did not affect TRAAK. Diethyl ether also decreased TASK activity.

Figure 4A:
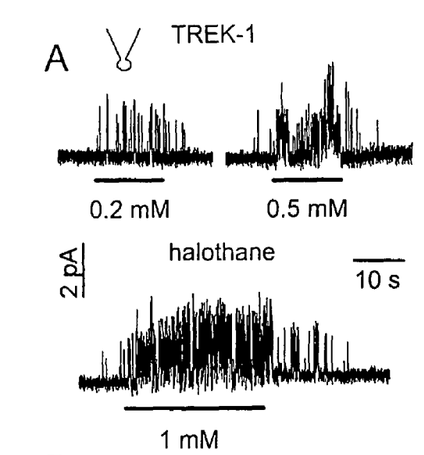
Figure 4B:
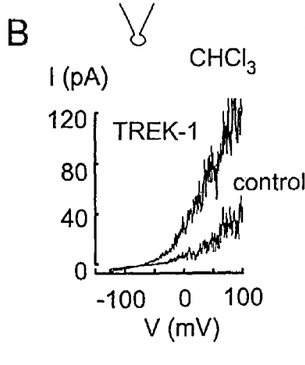
Figure 4C:
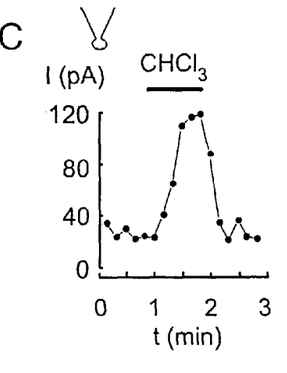
Figure 4D:
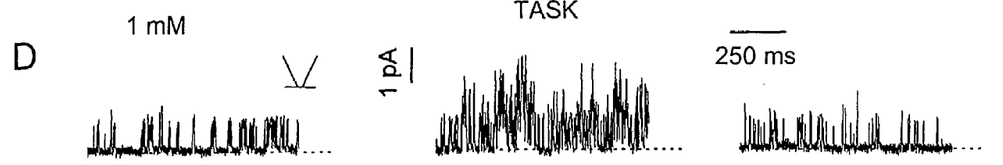
Figure 4E:
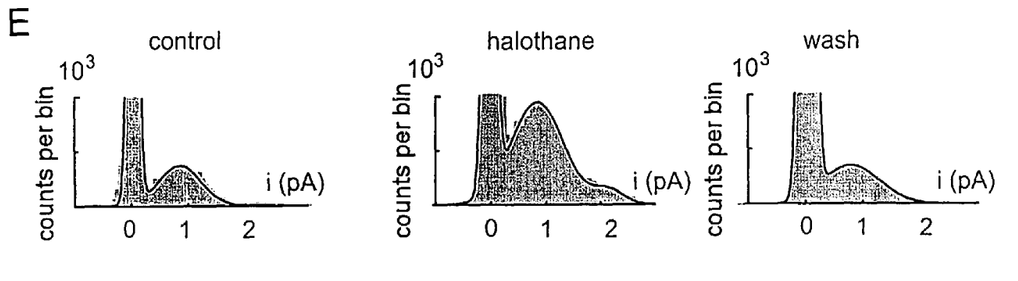

To demonstrate that activation by volatile anesthetics does not occur via second messenger pathways, experiments were conducted on excised patches. FIG. 4A shows that in an excised outside-out patch, halothane reversibly, and in a dose dependent manner, opened a 48 pS TREK-1 channel. No channel activity was observed in the absence of the anesthetic, suggesting that halothane converts inactive channels into active channels. The I-V curve of the chloroform-sensitive current in an outside-out patch shows the characteristic outward-going rectification previously observed in the macroscopic whole cell conditions, as shown in FIGS. 4B–4C and FIG. 1B (inset). As shown in FIGS. 4D–4E, in the inside-out patch configuration, halothane reversibly opened a 12 pS TASK channel. In the absence of anesthetics, a single TASK channel was opened, as shown in the left panels of FIGS. 4D–4E. The addition of halothane induced the opening of a second channel (see FIGS. 4D–4E middle panel) which closed again after washing (see right panel of FIGS. 4D and 4E). All the data, taken together, demonstrate that volatile general anesthetics open TASK and TREK-1 channels and that these effects are likely to be direct and independent of second messengers.

TREK-1 and TASK are probably critical channels for the action of general volatile anesthetics. Opening of these K+ channels along with the known modulation of neurotransmitter receptors will probably explain general anesthetic action. Effects of volatile anesthetics on ligand-gated ion channels such as GABA$_A$ receptors are probably particularly important at the post-synaptic level. Opening of background TREK-1 and TASK channels by volatile anesthetics might be very important both at the pre-synaptic ($I_{K(An)}$) and at the post-synaptic level. An activation of only a small fraction of these $I_{K(An)}$ channels will be expected to have significant effects on membrane polarization and consequently potentially important effects in both pre- and post-synaptic functions. TREK-1 and TASK channels are expressed in neuronal cells but they are also expressed in other tissues, and particularly in the heart. It is, therefore, not surprising that volatile anesthetics have depressive side-effects on heart function. These effects include a slowing of the heart rate and negative inotropic effects and are fully compatible with an exaggerate opening of background K+ channels by volatile anesthetics. The same considerations might very well explain ventilatory depression.

What is claimed is:

1. A method for identifying substances having anesthetic properties, wherein said substances produce a reversible state of unconsciousness with amnesia and analgesia in a mammal upon inhalation comprising:

(a) contacting said substances with TREK-1 having SEQ ID No. 2 or 4, or TASK having SEQ ID. No. 5, wherein said TREK-1 or TASK are mammalian potassium transport proteins, and wherein said TREK-1 or TASK protein exhibits outward-going potassium rectification; and (b) determining the potassium transport activity of said TREK-1 or TASK protein, wherein an activation of potassium transport is indicative of said substance having anesthetic properties.

2. The method of claim 1, wherein said substances are contacted with TASK.

3. The method of claim 1, wherein said substances are contacted with TREK-1.

4. A method for identifying substances having anesthetic properties, wherein said substances produce a reversible state of unconsciousness with concurrent amnesia and analgesia in a mammal upon inhalation comprising:

(a) contacting said substance with COS cells, wherein said COS cells are transfected with a nucleotide vector comprising a nucleic acid molecule encoding a potassium channel having two pore domains and four transmembrane segments, the potassium channel having an amino acid sequence selected from the group consisting of a TREK-1 protein having SEQ ID NO: 2 or SEQ ID NO: 4, wherein said COS cells transiently express said potassium channel on a surface of said COS cells, and wherein said potassium channel exhibits outward-going potassium rectification, and wherein said potassium channel is selectively activated by chloroform, diethyl ether, halothane or isoflurane; and (b) determining the potassium transport activity of said TREK-1 wherein an activation of potassium transport is indicative of said substance having said anesthetic properties.

5. A method for identifying substances having anesthetic properties, wherein said substances produce a reversible state of unconsciousness with concurrent amnesia and analgesia in a mammal upon inhalation comprising:

(a) contacting said substance with COS cells, wherein said COS cells are transfected with a nucleotide vector comprising a nucleic acid molecule encoding an amino acid sequence set forth in SEQ ID NO: 2, wherein said COS cells transiently express said amino acid sequence on a surface of said COS cells, and wherein said amino acid sequence exhibits outward-going potassium rectification; and (b) detemining the potassium transport activity of said amino acid sequence wherein an activation of potassium transport is indicative of said substance having said anesthetic properties.

6. A method for identifying substances having anesthetic properties, wherein said substances produce a reversible state of unconsciousness with concurrent amnesia and analgesia in a mammal upon inhalation comprising:

(a) contacting said substance with COS cells, wherein said COS cells are transfected with a nucleotide vector comprising a nucleic acid molecule encoding an amino acid sequence set forth in SEQ ID NO: 4, wherein said COS cells transiently express said amino acid sequence on a surface of said COS cells, and wherein said amino acid sequence exhibits outward-going potassium rectification; and (b) determining the potassium transport activity of said amino acid sequence wherein an activation of potassium transport is indicative of said substance having said anesthetic properties.

7. A method for identifying substances having anesthetic properties, wherein said substances produce a reversible state of unconsciousness with concurrent amnesia and analgesia in a mammal upon inhalation comprising:

(a) contacting said substance with transfected cells, wherein said transfected cells are transfected with a nucleotide vector comprising a nucleic acid molecule encoding a potassium channel, TASK, having an amino acid sequence of SEQ ID NO: 5, wherein said transfected cells transiently express said TASK on a surface of said transfected cells, and wherein said TASK exhibits outward-going potassium rectification, and wherein said TASK is selectively activated by halothane or isoflurane; and (b) determining the potassium transport activity of said TASK wherein an activation of potassium transport is indicative of said substance having said anesthetic properties.

8. A method for identifying substances having anesthetic properties, wherein said substances produce a reversible state of unconsciousness with concurrent amnesia and analgesia in a mammal upon inhalation comprising:
   (a) contacting said substance with transfected cells, witherein said transfected cells are transfected with a nucleotide vector comprising a nucleic acid molecule encoding SEQ ID NO: 5, wherein said transfected cells transiently express amino acid sequence on a surface of said transfected cells, and wherein said amnio acid sequence exhibits outward-going potassium rectification; and
   (b) determining the potassium transport activity of said amino acid sequence wherein an activation of potassium transport is indicative of said substance having said anesthetic properties.

9. The method of claim 7, wherein said transfected cells are selected from the group consisting of COS cells, HELA cells, *Spodoptera* cells, *Xenopus* oocytes, embryonic kidney cells, Chinese hamster ovary cells, and fibroblasts.

* * * * *

SEQUENCE LISTING

<160> NUMBER OF SEQ ID NOS: 5

<210> SEQ ID NO 1
<211> LENGTH: 1236
<212> TYPE: DNA
<213> ORGANISM: Homo sapiens
<220> FEATURE:
<221> NAME/KEY: CDS
<222> LOCATION: (1)..(1236)

<400> SEQUENCE: 1

```
atg gcg gcc cct gac ttg ctg gat cct aaa tct gcc gct cag aac tcc    48
Met Ala Ala Pro Asp Leu Leu Asp Pro Lys Ser Ala Ala Gln Asn Ser
 1               5                  10                  15 aaa ccg agg ctc tcg ttt tcc acg aaa ccc aca gtg ctt gct tcc cgg    96
Lys Pro Arg Leu Ser Phe Ser Thr Lys Pro Thr Val Leu Ala Ser Arg
            20                  25                  30 gtg gag agt gac acg acc att aat gtt atg aaa tgg aag acg gtc tcc   144
Val Glu Ser Asp Thr Thr Ile Asn Val Met Lys Trp Lys Thr Val Ser
        35                  40                  45 acg ata ttc ctg gtg gtt gtc ctc tat ctg atc atc gga gcc acc gtg   192
Thr Ile Phe Leu Val Val Val Leu Tyr Leu Ile Ile Gly Ala Thr Val
    50                  55                  60 ttc aaa gca ttg gag cag cct cat gag att tca cag agg acc acc att   240
Phe Lys Ala Leu Glu Gln Pro His Glu Ile Ser Gln Arg Thr Thr Ile
65                  70                  75                  80 gtg atc cag aag caa aca ttc ata tcc caa cat tcc tgt gtc aat tcg   288
Val Ile Gln Lys Gln Thr Phe Ile Ser Gln His Ser Cys Val Asn Ser
                85                  90                  95 acg gag ctg gat gaa ctc att cag caa ata gtg gca gca ata aat gca   336
Thr Glu Leu Asp Glu Leu Ile Gln Gln Ile Val Ala Ala Ile Asn Ala
            100                 105                 110 ggg att ata ccg tta gga aac acc tcc aat caa atc agt cac tgg gat   384
Gly Ile Ile Pro Leu Gly Asn Thr Ser Asn Gln Ile Ser His Trp Asp
        115                 120                 125 ttg gga agt tcc ttc ttt ttt gct ggc act gtt att aca acc ata gga   432
Leu Gly Ser Ser Phe Phe Phe Ala Gly Thr Val Ile Thr Thr Ile Gly
    130                 135                 140 ttt gga aac atc tca cca cgc aca gaa ggc ggc aaa ata ttc tgt atc   480
Phe Gly Asn Ile Ser Pro Arg Thr Glu Gly Gly Lys Ile Phe Cys Ile
145                 150                 155                 160 atc tat gcc tta ctg gga att ccc ctc ttt ggt ttc ctc ttg gct gga   528
Ile Tyr Ala Leu Leu Gly Ile Pro Leu Phe Gly Phe Leu Leu Ala Gly
                165                 170                 175 gtt gga gat cag cta ggc acc ata ttt gga aaa gga att gcc aaa gtg   576
Val Gly Asp Gln Leu Gly Thr Ile Phe Gly Lys Gly Ile Ala Lys Val
            180                 185                 190 gaa gat acg ttt att aag tgg aat gtt agt cag acc aag att cgc atc   624
Glu Asp Thr Phe Ile Lys Trp Asn Val Ser Gln Thr Lys Ile Arg Ile
        195                 200                 205 atc tca aca atc ata ttt ata cta ttt ggc tgt gta ctc ttt gtg gct   672
Ile Ser Thr Ile Ile Phe Ile Leu Phe Gly Cys Val Leu Phe Val Ala
    210                 215                 220 ctg cct gcg atc ata ttc aaa cac ata gaa ggc tgg agt gcc ctg gac   720
Leu Pro Ala Ile Ile Phe Lys His Ile Glu Gly Trp Ser Ala Leu Asp
225                 230                 235                 240
```

-continued

```
gcc att tat ttt gtg gtt atc act cta aca act att gga ttt ggt gac      768
Ala Ile Tyr Phe Val Val Ile Thr Leu Thr Thr Ile Gly Phe Gly Asp
            245                 250                 255 tac gtt gca ggt gga tcc gat att gaa tat ctg gac ttc tat aag cct      816
Tyr Val Ala Gly Gly Ser Asp Ile Glu Tyr Leu Asp Phe Tyr Lys Pro
        260                 265                 270 gtc gtg tgg ttc tgg atc ctt gta ggg ctt gct tac ttt gct gct gtc      864
Val Val Trp Phe Trp Ile Leu Val Gly Leu Ala Tyr Phe Ala Ala Val
    275                 280                 285 ctg agc atg att gga gat tgg ctc cga gtg ata tct aaa aag aca aaa      912
Leu Ser Met Ile Gly Asp Trp Leu Arg Val Ile Ser Lys Lys Thr Lys
290                 295                 300 gaa gag gtg gga gag ttc aga gca cac gct gct gag tgg aca gcc aac      960
Glu Glu Val Gly Glu Phe Arg Ala His Ala Ala Glu Trp Thr Ala Asn
305                 310                 315                 320 gtc aca gcc gaa ttc aaa gaa acc agg agg cga ctg agt gtg gag att     1008
Val Thr Ala Glu Phe Lys Glu Thr Arg Arg Arg Leu Ser Val Glu Ile
                325                 330                 335 tat gac aag ttc cag cgg gcc acc tcc atc aag cgg aag ctc tcg gca     1056
Tyr Asp Lys Phe Gln Arg Ala Thr Ser Ile Lys Arg Lys Leu Ser Ala
            340                 345                 350 gaa ctg gct gga aac cac aat cag gag ctg act cct tgt agg agg acc     1104
Glu Leu Ala Gly Asn His Asn Gln Glu Leu Thr Pro Cys Arg Arg Thr
        355                 360                 365 ctg tca gtg aac cac ctg acc aac gag agg gat gtc ttg cct ccc tta     1152
Leu Ser Val Asn His Leu Thr Asn Glu Arg Asp Val Leu Pro Pro Leu
    370                 375                 380 ctg aag act gag agt atc tat ctg aat ggt ttg acg cca cac tgt gct     1200
Leu Lys Thr Glu Ser Ile Tyr Leu Asn Gly Leu Thr Pro His Cys Ala
385                 390                 395                 400 ggt gaa gag att gct gtg att gag aac atc aaa tag                     1236
Gly Glu Glu Ile Ala Val Ile Glu Asn Ile Lys
                405                 410
```

<210> SEQ ID NO 2
<211> LENGTH: 411
<212> TYPE: PRT
<213> ORGANISM: Homo sapiens

<400> SEQUENCE: 2

```
Met Ala Ala Pro Asp Leu Leu Asp Pro Lys Ser Ala Ala Gln Asn Ser
  1               5                  10                  15

Lys Pro Arg Leu Ser Phe Ser Thr Lys Pro Thr Val Leu Ala Ser Arg
             20                  25                  30

Val Glu Ser Asp Thr Thr Ile Asn Val Met Lys Trp Lys Thr Val Ser
         35                  40                  45

Thr Ile Phe Leu Val Val Val Leu Tyr Leu Ile Ile Gly Ala Thr Val
     50                  55                  60

Phe Lys Ala Leu Glu Gln Pro His Glu Ile Ser Gln Arg Thr Thr Ile
 65                  70                  75                  80

Val Ile Gln Lys Gln Thr Phe Ile Ser Gln His Ser Cys Val Asn Ser
                 85                  90                  95

Thr Glu Leu Asp Glu Leu Ile Gln Gln Ile Val Ala Ala Ile Asn Ala
            100                 105                 110

Gly Ile Ile Pro Leu Gly Asn Thr Ser Asn Gln Ile Ser His Trp Asp
        115                 120                 125

Leu Gly Ser Ser Phe Phe Phe Ala Gly Thr Val Ile Thr Thr Ile Gly
    130                 135                 140
```

-continued

```
Phe Gly Asn Ile Ser Pro Arg Thr Glu Gly Gly Lys Ile Phe Cys Ile
145                 150                 155                 160

Ile Tyr Ala Leu Leu Gly Ile Pro Leu Phe Gly Phe Leu Leu Ala Gly
                165                 170                 175

Val Gly Asp Gln Leu Gly Thr Ile Phe Gly Lys Gly Ile Ala Lys Val
            180                 185                 190

Glu Asp Thr Phe Ile Lys Trp Asn Val Ser Gln Thr Lys Ile Arg Ile
        195                 200                 205

Ile Ser Thr Ile Ile Phe Ile Leu Phe Gly Cys Val Leu Phe Val Ala
    210                 215                 220

Leu Pro Ala Ile Ile Phe Lys His Ile Glu Gly Trp Ser Ala Leu Asp
225                 230                 235                 240

Ala Ile Tyr Phe Val Val Ile Thr Leu Thr Thr Ile Gly Phe Gly Asp
                245                 250                 255

Tyr Val Ala Gly Gly Ser Asp Ile Glu Tyr Leu Asp Phe Tyr Lys Pro
            260                 265                 270

Val Val Trp Phe Trp Ile Leu Val Gly Leu Ala Tyr Phe Ala Ala Val
        275                 280                 285

Leu Ser Met Ile Gly Asp Trp Leu Arg Val Ile Ser Lys Lys Thr Lys
    290                 295                 300

Glu Glu Val Gly Glu Phe Arg Ala His Ala Ala Glu Trp Thr Ala Asn
305                 310                 315                 320

Val Thr Ala Glu Phe Lys Glu Thr Arg Arg Arg Leu Ser Val Glu Ile
                325                 330                 335

Tyr Asp Lys Phe Gln Arg Ala Thr Ser Ile Lys Arg Lys Leu Ser Ala
            340                 345                 350

Glu Leu Ala Gly Asn His Asn Gln Glu Leu Thr Pro Cys Arg Arg Thr
        355                 360                 365

Leu Ser Val Asn His Leu Thr Asn Glu Arg Asp Val Leu Pro Pro Leu
    370                 375                 380

Leu Lys Thr Glu Ser Ile Tyr Leu Asn Gly Leu Thr Pro His Cys Ala
385                 390                 395                 400

Gly Glu Glu Ile Ala Val Ile Glu Asn Ile Lys
                405                 410

<210> SEQ ID NO 3
<211> LENGTH: 3580
<212> TYPE: DNA
<213> ORGANISM: Mus musculus
<220> FEATURE:
<221> NAME/KEY: CDS
<222> LOCATION: (484)..(1719)

<400> SEQUENCE: 3
agagcggcga ggcgagggga gagtggtgct acgggccagg cgggccaccc cgggccacac      60
ccccaccttg cgggcgcccg gcggggctcg agccaggcgg ggcgcctcac aaagacatgc     120 gaagagggc tgcagtgatc accccctcgc tgagccccgg ggcagagccc agccgccggc     180
cgagcgcacg gagccacggg ccgagcgcac ccagggcccg cgcgggaccc caggcggcca     240
cgcaatcggg gtgacccatc gcgcgcgggg gcgtcgtcgt ccgatcccaa cttggcctcg     300
gcctcgccct ctgcccagcc tgccaccgct ggtgtcctct ccttccggcg atttcgtttc     360
ttctcacgct cccccctcta tacccctccc gctccagcc ccgctctccc caccttgtaa      420
aacaaagccg gggaaaatgc ctacccgtgc agctcggagc gcgcagcccg tcttggaata     480
```

-continued

| | |
|---|---|
| agg atg gcg gcc cct gac ttg ctg gat ccc aag tct gct gct cag aac<br>Arg Met Ala Ala Pro Asp Leu Leu Asp Pro Lys Ser Ala Ala Gln Asn<br>1                        5                      10                  15 | 528 |
| tcc aaa ccg agg ctc tca ttc tcc tca aaa ccc acc gtg ctt gct tcc<br>Ser Lys Pro Arg Leu Ser Phe Ser Ser Lys Pro Thr Val Leu Ala Ser<br>                   20                     25                     30 | 576 |
| cgg gtg gag agt gac tcg gcc att aat gtt atg aaa tgg aag aca gtc<br>Arg Val Glu Ser Asp Ser Ala Ile Asn Val Met Lys Trp Lys Thr Val<br>             35                     40                     45 | 624 |
| tcc acg att ttc ctg gtg gtc gtc ctc tac ctg atc atc gga gcc gcg<br>Ser Thr Ile Phe Leu Val Val Val Leu Tyr Leu Ile Ile Gly Ala Ala<br>        50                     55                     60 | 672 |
| gtg ttc aag gca ttg gag cag cct cag gag att tcc cag agg acc acc<br>Val Phe Lys Ala Leu Glu Gln Pro Gln Glu Ile Ser Gln Arg Thr Thr<br>65                     70                     75 | 720 |
| att gtg atc cag aag cag acc ttc ata gcc cag cat gcc tgc gtc aac<br>Ile Val Ile Gln Lys Gln Thr Phe Ile Ala Gln His Ala Cys Val Asn<br>80                     85                     90                     95 | 768 |
| tcc acc gag ctg gac gaa ctc atc cag caa ata gtg gca gca ata aac<br>Ser Thr Glu Leu Asp Glu Leu Ile Gln Gln Ile Val Ala Ala Ile Asn<br>                     100                    105                    110 | 816 |
| gca ggg att atc ccc tta gga aac agc tcc aat caa gtt agt cac tgg<br>Ala Gly Ile Ile Pro Leu Gly Asn Ser Ser Asn Gln Val Ser His Trp<br>             115                    120                    125 | 864 |
| gac ctc gga agc tct ttc ttc ttt gct ggt act gtt atc aca acc ata<br>Asp Leu Gly Ser Ser Phe Phe Phe Ala Gly Thr Val Ile Thr Thr Ile<br>        130                    135                    140 | 912 |
| gga ttt gga aac atc tcc cca cga act gaa ggt gga aaa ata ttc tgc<br>Gly Phe Gly Asn Ile Ser Pro Arg Thr Glu Gly Gly Lys Ile Phe Cys<br>145                    150                    155 | 960 |
| atc atc tat gcc ttg ctg gga att ccc ctc ttt ggc ttt cta ctg gct<br>Ile Ile Tyr Ala Leu Leu Gly Ile Pro Leu Phe Gly Phe Leu Leu Ala<br>160                    165                    170                    175 | 1008 |
| ggg gtt ggt gat cag cta gga act ata ttt gga aaa gga att gcc aaa<br>Gly Val Gly Asp Gln Leu Gly Thr Ile Phe Gly Lys Gly Ile Ala Lys<br>                     180                    185                    190 | 1056 |
| gtg gaa gac aca ttt att aag tgg aat gtt agt cag acg aag att cgt<br>Val Glu Asp Thr Phe Ile Lys Trp Asn Val Ser Gln Thr Lys Ile Arg<br>             195                    200                    205 | 1104 |
| atc atc tcc acc atc atc ttc atc ctg ttt ggc tgt gtc ctc ttt gtg<br>Ile Ile Ser Thr Ile Ile Phe Ile Leu Phe Gly Cys Val Leu Phe Val<br>        210                    215                    220 | 1152 |
| gct ctc cct gcg gtc ata ttc aag cac ata gaa ggc tgg agc gcc ctg<br>Ala Leu Pro Ala Val Ile Phe Lys His Ile Glu Gly Trp Ser Ala Leu<br>225                    230                    235 | 1200 |
| gac gct atc tat ttt gtg gtt atc act ctg acg acc att gga ttt gga<br>Asp Ala Ile Tyr Phe Val Val Ile Thr Leu Thr Thr Ile Gly Phe Gly<br>240                    245                    250                    255 | 1248 |
| gac tac gtg gca ggt gga tca gac att gaa tat ctg gac ttc tac aag<br>Asp Tyr Val Ala Gly Gly Ser Asp Ile Glu Tyr Leu Asp Phe Tyr Lys<br>                   260                    265                    270 | 1296 |
| cct gtg gtg tgg ttc tgg atc ctc gtt ggg ctg gcc tac ttt gca gct<br>Pro Val Val Trp Phe Trp Ile Leu Val Gly Leu Ala Tyr Phe Ala Ala<br>             275                    280                    285 | 1344 |
| gtt ctg agc atg att ggg gac tgg cta cgg gtg atc tct aag aag acg<br>Val Leu Ser Met Ile Gly Asp Trp Leu Arg Val Ile Ser Lys Lys Thr<br>        290                    295                    300 | 1392 |
| aag gaa gag gtg gga gag ttc aga gcg cat gcc gct gag tgg aca gcc<br>Lys Glu Glu Val Gly Glu Phe Arg Ala His Ala Ala Glu Trp Thr Ala<br>305                     310                    315 | 1440 |

```
aat gtc acg gcc gag ttc aag gaa acg agg agg cgg ctg agc gtg gag    1488
Asn Val Thr Ala Glu Phe Lys Glu Thr Arg Arg Arg Leu Ser Val Glu
320                 325                 330                 335 atc tac gac aag ttc cag cgt gcc aca tcc gtg aag cgg aag ctc tcc    1536
Ile Tyr Asp Lys Phe Gln Arg Ala Thr Ser Val Lys Arg Lys Leu Ser
                340                 345                 350 gca gag ctg gcg ggc aac cac aac cag gaa ctg act ccg tgt agg agg    1584
Ala Glu Leu Ala Gly Asn His Asn Gln Glu Leu Thr Pro Cys Arg Arg
        355                 360                 365 acc ctg tct gtg aac cac ctg acc agc gag agg gaa gtc ctg cct ccc    1632
Thr Leu Ser Val Asn His Leu Thr Ser Glu Arg Glu Val Leu Pro Pro
370                 375                 380 ttg ctg aag gct gag agc atc tat ctg aac ggt ctg aca cca cac tgt    1680
Leu Leu Lys Ala Glu Ser Ile Tyr Leu Asn Gly Leu Thr Pro His Cys
                385                 390                 395 gct ggt gag gac ata gct gtc att gag aac atg aag tag ccctctcttg    1729
Ala Gly Glu Asp Ile Ala Val Ile Glu Asn Met Lys
400                 405                 410 gaagagtctg aggtggagcc atagggaagg gcttctctag gctctttgtg actgttgccg   1789
gtagcattta acattgtgc atggtgacct caaagggaaa gcaaatagaa acacccatc    1849 tggtcacctt acatccaggg agggtgttgt cccgaggcgg cactctgagg atgccgtgtg   1909
ctgtccgctg agtgctgagt gatggacagg cagtgtctga tgccttttgt gcccagactg   1969 tttccctcc ccctctctcc taacgtgcca taaggcctat gaatgaatct gaatgctttg    2029
ctggtcatgt agattggagg gatcagccct tggtttttca tggttcacct aactgagcct   2089
ggatactgac cacttaggga tgacaacatt tcttttgta aatggcgaga aattcttacg    2149 cagccttta cctaagaaat tttctgccag tgccttatct tatgaagaaa caagaccctg    2209
tctggtgggc ttgtggttcc tcccttcccc gccctcaccg tgggctcacc ctttgctgac   2269
tctcacctat ccctcccct ccgcatacct tattgtgctg gaagcaatgt gtggcttgat    2329
ggaagaaaca gatgccaact gcaggcacag aagcaacatg gaagctctgg cgtcacgggc   2389
actgcagaga agggaggtca gagaaggccc tctgagtat ttatttgacc ggggtaccaa    2449
tggtacagct atatatatgt acagagtaat aattcccagg ccggtaacct tggctgcttc   2509
cacacggccc cctttttcc ctggcagtat ttgaagttta tcattatta ataactagtc     2569 atttttaaag gcagaagaag acatgagcac atacatctgt aatctacgtg atgtgataag   2629
aaaactgttc agactggtat tgcaaggtga tctcagacag tcgatatgga ttcattctga   2689
tgagaagaaa acagcgagac cacgtgtcgt gcgcatgagc tcatacaggg ctcactgtca   2749
gcttggacca gcccgtgagg tacagcaggc ttacacactt tcttttctta agtggttctt   2809
gccaaactgg agggagggc gatgcccttc agaagggggc acagcccag ccagcccagg     2869 gtccctctgt ggtcatgact gggtgtgagc acagatgctg gccttgggat cactgtgagt   2929
tttgcacatg gagagataca gactgctggc ataggtcgtc tctaacagta gagaaaacgc   2989
cgattagcac aatctaaatc ccccgagtag cttttgttt aggataagag aaggctggta    3049
attcacttaa tttaaattta tatcctataa ttcttttgg atgtttcaag attcagaaaa    3109
agtccagtcc ctgcatctag caaaccgccg cccttcctc tgtgcccgta cttacatcta    3169
ctgaacactg tatatgtaat tttttaaattt taaagcgca gaaggaaaat gattcttcta   3229
catgtaatcg caaaactgat ttctcccttc tgggggaggc ttgggcttac gtgatcatgt   3289
ggcattcaga gtaaagtctt aagacataaa cccaggatgt ttaaaaacac aaaaagattc   3349
```

-continued

```
ctatttcca aaatttgaat ttaagctata aatgtaaata tatccagttc gcttgcagag    3409
agtactttta taaacctatg aagattctaa ccaaaatttt aaaatgtcgg gttcctttac    3469
aaagaaagct ccacccatct cctgaatagc cgttttggaa gctgacatgg tgggatgtac    3529
cacgtataaa ctgtgaactg gaggacaaat aaagtttgta attaaaaaaa a             3580
```

<210> SEQ ID NO 4
<211> LENGTH: 411
<212> TYPE: PRT
<213> ORGANISM: Mus musculus

<400> SEQUENCE: 4

```
Met Ala Ala Pro Asp Leu Leu Asp Pro Lys Ser Ala Ala Gln Asn Ser
  1               5                  10                  15

Lys Pro Arg Leu Ser Phe Ser Ser Lys Pro Thr Val Leu Ala Ser Arg
             20                  25                  30

Val Glu Ser Asp Ser Ala Ile Asn Val Met Lys Trp Lys Thr Val Ser
         35                  40                  45

Thr Ile Phe Leu Val Val Val Leu Tyr Leu Ile Ile Gly Ala Ala Val
     50                  55                  60

Phe Lys Ala Leu Glu Gln Pro Gln Glu Ile Ser Gln Arg Thr Thr Ile
 65                  70                  75                  80

Val Ile Gln Lys Gln Thr Phe Ile Ala Gln His Ala Cys Val Asn Ser
                 85                  90                  95

Thr Glu Leu Asp Glu Leu Ile Gln Gln Ile Val Ala Ala Ile Asn Ala
            100                 105                 110

Gly Ile Ile Pro Leu Gly Asn Ser Ser Asn Gln Val Ser His Trp Asp
        115                 120                 125

Leu Gly Ser Ser Phe Phe Phe Ala Gly Thr Val Ile Thr Thr Ile Gly
130                 135                 140

Phe Gly Asn Ile Ser Pro Arg Thr Glu Gly Gly Lys Ile Phe Cys Ile
145                 150                 155                 160

Ile Tyr Ala Leu Leu Gly Ile Pro Leu Phe Gly Phe Leu Leu Ala Gly
                165                 170                 175

Val Gly Asp Gln Leu Gly Thr Ile Phe Gly Lys Gly Ile Ala Lys Val
            180                 185                 190

Glu Asp Thr Phe Ile Lys Trp Asn Val Ser Gln Thr Lys Ile Arg Ile
        195                 200                 205

Ile Ser Thr Ile Ile Phe Ile Leu Phe Gly Cys Val Leu Phe Val Ala
    210                 215                 220

Leu Pro Ala Val Ile Phe Lys His Ile Glu Gly Trp Ser Ala Leu Asp
225                 230                 235                 240

Ala Ile Tyr Phe Val Val Ile Thr Leu Thr Thr Ile Gly Phe Gly Asp
                245                 250                 255

Tyr Val Ala Gly Gly Ser Asp Ile Glu Tyr Leu Asp Phe Tyr Lys Pro
            260                 265                 270

Val Val Trp Phe Trp Ile Leu Val Gly Leu Ala Tyr Phe Ala Ala Val
        275                 280                 285

Leu Ser Met Ile Gly Asp Trp Leu Arg Val Ile Ser Lys Lys Thr Lys
    290                 295                 300

Glu Glu Val Gly Glu Phe Arg Ala His Ala Ala Glu Trp Thr Ala Asn
305                 310                 315                 320

Val Thr Ala Glu Phe Lys Glu Thr Arg Arg Arg Leu Ser Val Glu Ile
                325                 330                 335
```

```
Tyr Asp Lys Phe Gln Arg Ala Thr Ser Val Lys Arg Lys Leu Ser Ala
                340                 345                 350

Glu Leu Ala Gly Asn His Asn Gln Glu Leu Thr Pro Cys Arg Arg Thr
            355                 360                 365

Leu Ser Val Asn His Leu Thr Ser Glu Arg Glu Val Leu Pro Pro Leu
        370                 375                 380

Leu Lys Ala Glu Ser Ile Tyr Leu Asn Gly Leu Thr Pro His Cys Ala
385                 390                 395                 400

Gly Glu Asp Ile Ala Val Ile Glu Asn Met Lys
                405                 410

<210> SEQ ID NO 5
<211> LENGTH: 394
<212> TYPE: PRT
<213> ORGANISM: Mus sp.
<220> FEATURE:
<223> OTHER INFORMATION: TASK

<400> SEQUENCE: 5

Met Lys Arg Gln Asn Val Arg Thr Leu Ala Leu Ile Val Cys Thr Phe
 1               5                  10                  15

Thr Tyr Leu Leu Val Gly Ala Ala Val Phe Asp Ala Leu Glu Ser Glu
            20                  25                  30

Pro Glu Leu Ile Glu Arg Gln Arg Leu Glu Leu Arg Gln Gln Glu Leu
        35                  40                  45

Arg Ala Arg Tyr Asn Leu Ser Gln Gly Gly Tyr Glu Glu Leu Glu Arg
    50                  55                  60

Val Val Leu Arg Leu Lys Pro His Lys Ala Gly Val Gln Trp Arg Phe
65                  70                  75                  80

Ala Gly Ser Phe Tyr Phe Ala Ile Thr Val Ile Thr Thr Ile Gly Tyr
                85                  90                  95

Gly His Ala Ala Pro Ser Thr Asp Gly Gly Lys Val Phe Cys Met Phe
            100                 105                 110

Tyr Ala Leu Leu Gly Ile Pro Leu Thr Leu Val Met Phe Gln Ser Leu
        115                 120                 125

Gly Glu Arg Ile Asn Thr Leu Val Arg Tyr Leu Leu His Arg Ala Lys
    130                 135                 140

Lys Gly Leu Gly Met Arg Arg Ala Asp Val Ser Met Ala Asn Met Val
145                 150                 155                 160

Leu Ile Gly Phe Phe Ser Cys Ile Ser Thr Leu Cys Ile Gly Ala Ala
                165                 170                 175

Ala Phe Ser His Tyr Glu His Trp Thr Phe Phe Gln Ala Tyr Tyr Tyr
            180                 185                 190

Cys Phe Ile Thr Leu Thr Thr Ile Gly Phe Gly Asp Tyr Val Ala Leu
        195                 200                 205

Gln Lys Asp Gln Ala Leu Gln Thr Gln Pro Gln Tyr Val Ala Phe Ser
    210                 215                 220

Phe Val Tyr Ile Leu Thr Gly Leu Thr Val Ile Gly Ala Phe Leu Asn
225                 230                 235                 240

Leu Val Val Leu Arg Phe Met Thr Met Asn Ala Glu Asp Glu Lys Arg
                245                 250                 255

Asp Ala Glu His Arg Ala Leu Leu Thr Arg Asn Gly Gln Ala Gly Gly
            260                 265                 270

Gly Gly Gly Gly Gly Ser Ala His Thr Thr Asp Thr Ala Ser Ser Thr
        275                 280                 285
```

```
                                    -continued
Ala Ala Ala Gly Gly Gly Gly Phe Arg Asn Val Tyr Ala Glu Val Leu
    290             295             300
His Phe Gln Ser Met Cys Ser Cys Leu Trp Tyr Lys Ser Arg Glu Lys
305             310              315             320
Leu Gln Tyr Ser Ile Pro Met Ile Ile Pro Arg Asp Leu Ser Thr Ser
                325             330              335
Asp Thr Cys Val Glu Gln Ser His Ser Ser Pro Gly Gly Gly Gly Arg
            340             345              350
Tyr Ser Asp Thr Pro Ser Arg Arg Cys Leu Cys Ser Gly Ala Pro Arg
        355             360              365
Ser Ala Ile Ser Ser Val Ser Thr Gly Leu His Ser Leu Ser Thr Phe
    370             375              380
Arg Gly Leu Met Lys Arg Ser Ser Val
385             390
```